(12) United States Patent
Simard et al.

(10) Patent No.: US 8,461,294 B2
(45) Date of Patent: Jun. 11, 2013

(54) NUCLEOPHILIC SUBSTITUTION OF CARBON NANOTUBES

(75) Inventors: Benoit Simard, Orleans (CA); Jingwen Guan, Ottawa (CA)

(73) Assignee: National Research Council of Canada, Ottawa (CA)

( * ) Notice: Subject to any disclaimer, the term of this patent is extended or adjusted under 35 U.S.C. 154(b) by 640 days.

(21) Appl. No.: 12/528,959

(22) PCT Filed: Feb. 28, 2008

(86) PCT No.: PCT/CA2008/000388
§ 371 (c)(1),
(2), (4) Date: Dec. 4, 2009

(87) PCT Pub. No.: WO2008/104079
PCT Pub. Date: Sep. 4, 2008

(65) Prior Publication Data
US 2010/0087614 A1    Apr. 8, 2010

Related U.S. Application Data

(60) Provisional application No. 60/903,838, filed on Feb. 28, 2007.

(51) Int. Cl.
*C08G 65/04*    (2006.01)
(52) U.S. Cl.
USPC .............................. 528/421; 977/746; 977/847
(58) Field of Classification Search
USPC ................................... 528/421; 977/746, 847
See application file for complete search history.

(56) References Cited

U.S. PATENT DOCUMENTS

| 7,691,359 | B2* | 4/2010 | Tour et al. ................... | 423/447.2 |
| 7,695,769 | B2* | 4/2010 | Watanabe et al. ........... | 427/372.2 |
| 7,700,063 | B2* | 4/2010 | Penicaud et al. ............ | 423/447.1 |
| 8,288,457 | B2* | 10/2012 | Simard et al. ................ | 523/468 |
| 2004/0071624 | A1* | 4/2004 | Tour et al. ................... | 423/447.1 |
| 2005/0170169 | A1* | 8/2005 | Watanabe et al. ............. | 428/323 |
| 2005/0207963 | A1 | 9/2005 | Tour et al. | |

(Continued)

FOREIGN PATENT DOCUMENTS

| GB | 241237 B | 9/2005 |
| WO | 02060812 | 8/2002 |
| WO | WO 2005/073127 | 8/2005 |
| WO | 2005090233 | 9/2005 |

OTHER PUBLICATIONS

Ajayan et al., "Single-Step in Situ Synthesis of Polymer-Grafted Single-Wall Nanotube Composites", J. Am. Chem. Soc. 9 vol. 125, No. 31, 2003 9259.

(Continued)

*Primary Examiner* — Mark Eashoo
*Assistant Examiner* — Megan McCulley
(74) *Attorney, Agent, or Firm* — McMillan LLP

(57) ABSTRACT

Compounds are attached to carbon nanotubes (CNT) by a process which comprises: subjecting surface treated CNTs which have been treated to induce negatively charged surface groups thereon, to nucleophilic substitution reaction with a compound carrying a functional group capable of reacting with the negatively charged groups on the CNT surface, whereby the compound chemically bonds to the CNT. The surface CNT treatment may be reduction. The compounds which are bonded to the CNT may be epoxy resins, bonded directly or through a spacer group. Bi-functional CNTs, grafted to both epoxy resins and other polymers such as polystyrene, are also made by this process.

2 Claims, 6 Drawing Sheets

U.S. PATENT DOCUMENTS

| | | | |
|---|---|---|---|
| 2006/0166003 A1 | 7/2006 | Khabashesku et al. | |
| 2007/0259994 A1* | 11/2007 | Tour et al. | 523/333 |
| 2009/0301896 A1* | 12/2009 | Tour et al. | 205/432 |
| 2010/0137502 A1* | 6/2010 | Watanabe et al. | 524/555 |
| 2011/0112287 A1* | 5/2011 | Balaban et al. | 540/122 |
| 2012/0065309 A1* | 3/2012 | Agrawal et al. | 524/155 |

OTHER PUBLICATIONS

Barron et al., "Solubilizaton of Single-Wall Carbon Nanotubes in Organic Solvents Without", Journal of Nanoscience and Nanotechnology, pp. 1533-4880, 2007.

Billups et al.,"In situ Raman Studies on Lithiated Single-Wall Carbon Nanotues in Liquid Ammonia", Chemical Physics Letters 410 (2005) 467-470.

Byrne et al., "Chemical Functionalization of Carbon Nanotubes for the Mechanical Reinforcement of Polystyrene Composites", Nanotechnology 19 (2008) 415707.

Hirsch et al., "Preferred Functionalization of Metallic and Small-Diameter Single-Walled Carbon Nanotubes by Nucleophilic Addition of Organolithium and- Magnesium Compounds Followed by Reoxidation", Chem. Eur. J. 2008, 14, 1607-1614.

Hirsch et al., "Covalent Sidewall Functionalization of SWNTs by Nucleophilic Addition of Lithium Amides", Eur. J. Org. Chem. 2008, 2544-2550.

Hirsch et al., "A Novel Diameter-Selective Functionalization of SWCNTs with Lithium Alkynylides", Eur. J. Org. Chem. 2010, 1494-1501.

Li et al., "Alkylation and Arylation of Single-Walled Carbon Nanotubes by Mechanochemical Method", Chemical Physics Letters 444 (2007) 258-262.

Liang et al., "In Situ Polymerization Initiated by Single-Walled Carbon Nanotube Salts", Chem. Mater., vol. 18, No. 20, 2006 4765.

Matrab et al., "Atom Transfer Radical Polymerization (ATRP) Initiated by Aryl Diazonium Salts: A New Route for Surface Modification of Multiwalled Carbon Nanotubes by Tethered Polymer Chains", Colloids and Surfaces A: Physicochem. Eng. Aspects 287 (2006) 217-221.

Qin et al., "Functionalization of Single-Walled Carbon Nanotubes with Polystyrene via Grafting to and Grafting from Methods", Macromolecules, vol. 37, No. 3, 2004.

Qin et al., "Covalent Cross-Linked Polymer/Single-Wall Carbon Nanotube Multilayer Films", Chem. Mater., vol. 17, No. 8, 2005.

Roubeau et al., "Covalent Functionalization of Carbon Nanotubes Through Organometallic Reduction and Electrophilic Attack", Journal of Nanoscience and Nanothechnology vol. 7, 3509-3513, 2007.

Vigolo et al., "Direct Revealing of the Occupation Sites of Heavy Alkali Metal Atoms in Single-Walled Carbon Nanotube Intercalation Compounds", J. Phys. Chem. C, vol. xxx, No. xx, XXXX, 2009.

Wei et al., "Covalent Sidewall Functionalization of Single-Walled Carbon Nanotubes Via One-Electron Reduction of Benzophenone by Potassium", Chemical Physics Letters 446 (2007) 142-144.

Xia et al., "Polymer-Encapsulated Carbon Nanotubes Prepared through Ultrasonically Initiated In Situ Emulsion Polymerization", Chem. Mater., vol. 15, No. 20, 2003.

Xia et al., "Single-Step in Situ Preparation of Polymer-Grafted Multi-Walled Carbon Nanotube Composites under 60Co ç-Ray Irradiation", Chem. Mater., vol. 18, No. 13, 2006.

Zhu et al., "Improving the Dispersion and Integration of Single-Walled Carbon Nanotubes in Epoxy Composites through Functionalization", Nano Lett., vol. 3, No. 8, 2003.

Covalent Surface Chemistry of Single-Walled Carbon Nanotubes, Banerjee, S.; Hermraj-Benny, T. and Wong S. S., Adv. Mater., 2005, 17, No. 1, pp. 17-29.

Chemistry of Carbon Nanotubes, Tasis, D.; Tagmatarachis, N.; Bianco, A. and Prato M. Chem. Rev., 2006, 106, 1105-1136.

Billups et al.,Org. Lett.,5, 1471 (2003).

Margrave et al., Nanolett., 3, 1107 (2003).

Penicaud et al. JACS 127, 8 (2005).

Tour et al. Chem. Mat., 13, 3823 (2001).

Liang, NanoLett., 4, 1257 (2004).

* cited by examiner

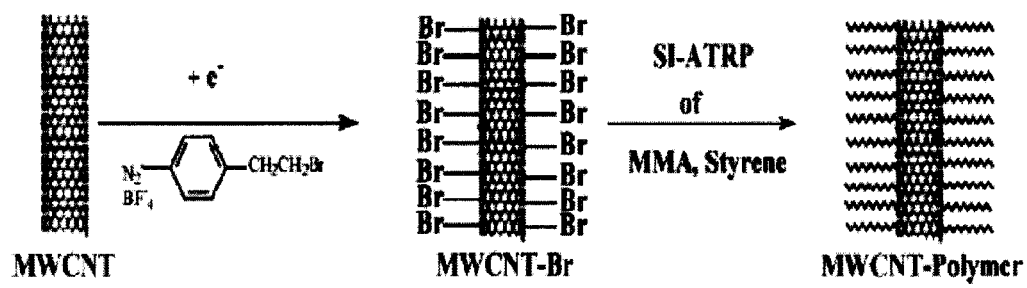
FIGURE 11 - Prior Art
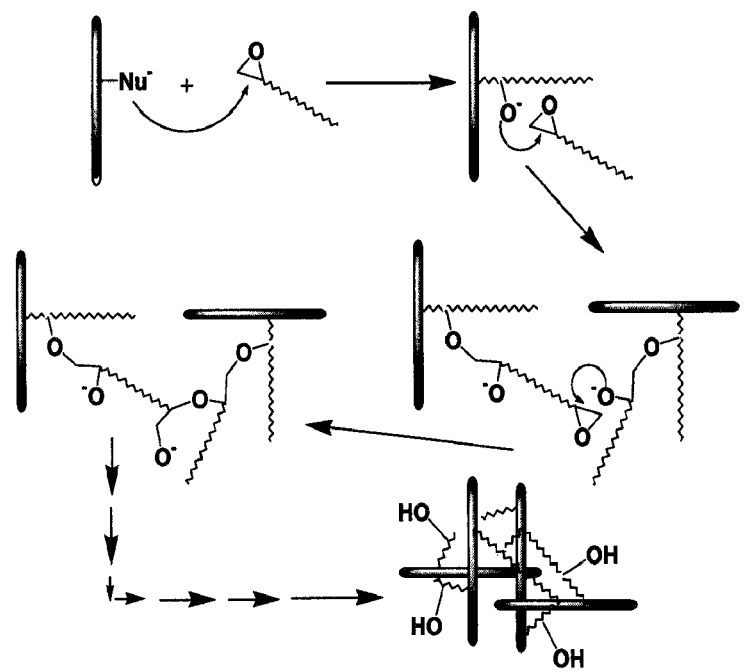
FIGURE 1

Molecule used for the n-doping:
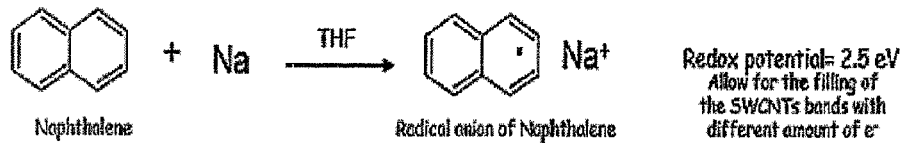
N-doping of the SWCNTs when the two phases are brought into contact
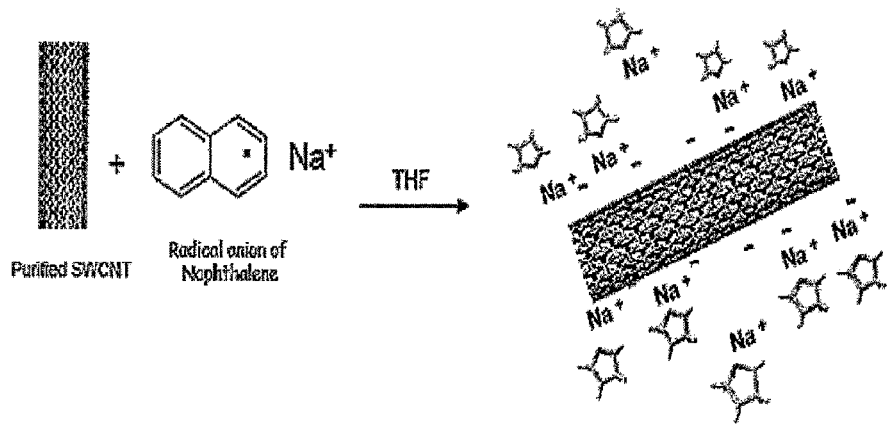
A. Penicaud, P. Poulin,† A. Derre, E. Anglaret, and P. Petit, J. AM. CHEM. SOC. 2005, 127, 8-9
FIGURE 2 - Prior Art
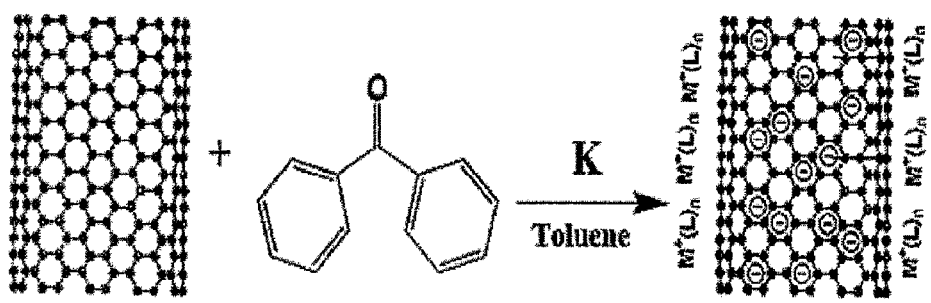
FIGURE 3

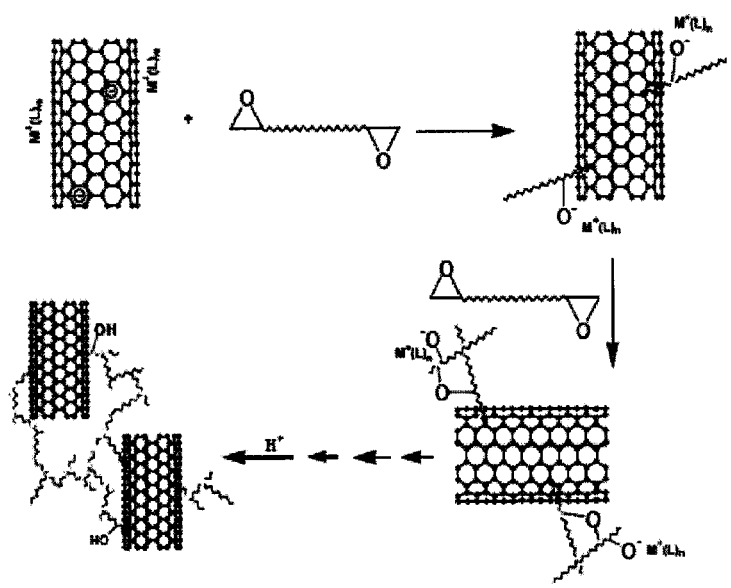
FIGURE 4
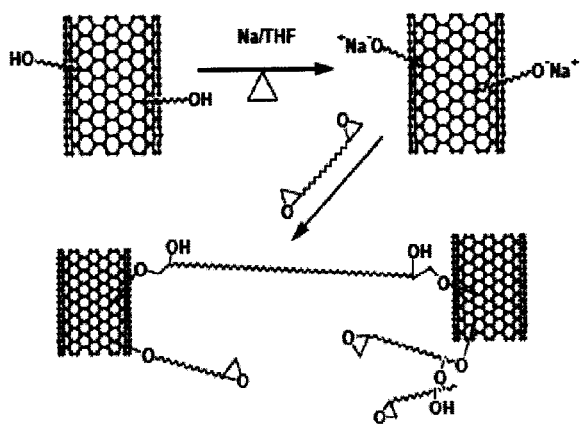
FIGURE 5
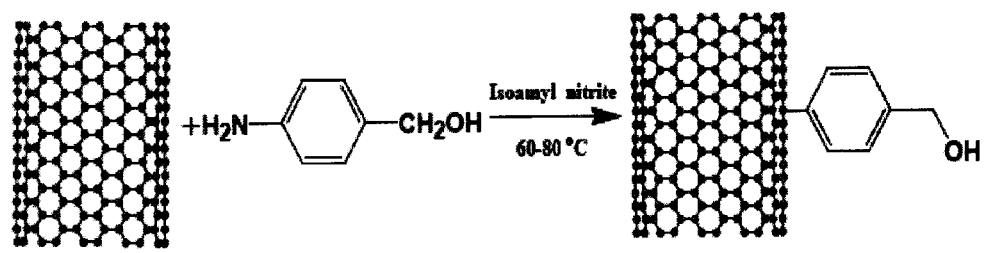
FIGURE 6 - Prior Art

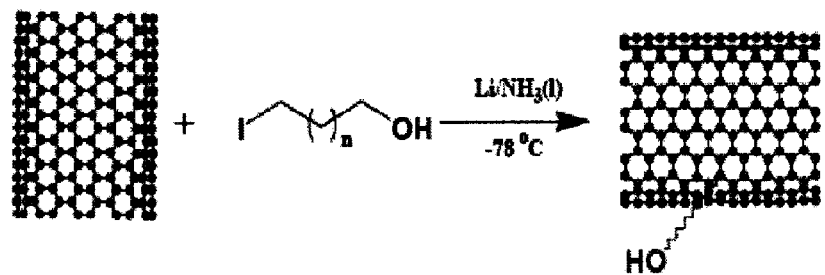
FIGURE 7 - Prior Art
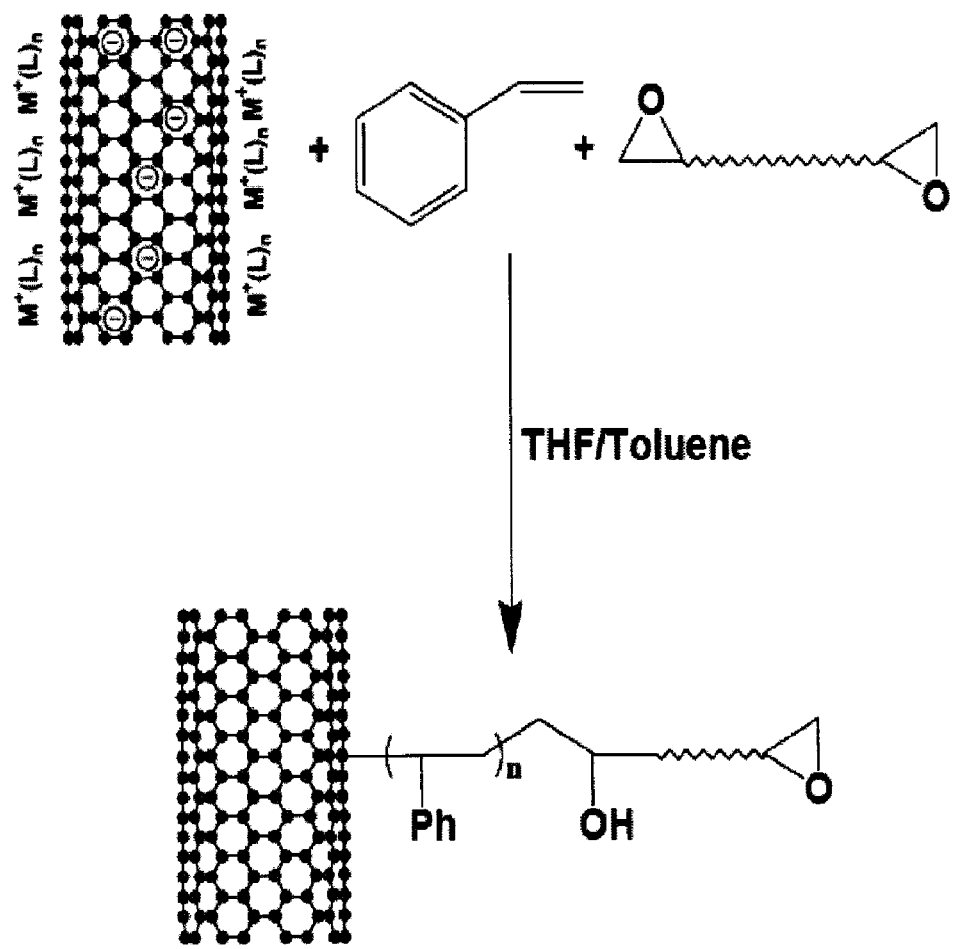
FIGURE 8

NUCLEOPHILIC SUBSTITUTION OF CARBON NANOTUBES

FIELD OF THE INVENTION

This invention relates to the field of nanotechnology. More particularly, it relates to carbon nanotubes, and to methods of attaching carbon nanotubes to structural materials such as epoxy resins.

BACKGROUND OF THE INVENTION

Carbon nanotubes (CNTs) are hollow carbon architectures made of concentric graphene sheets. They exhibit exceptional mechanical, electrical and thermal properties; the best of any known material. Combined with their very high aspect ratios that can reach well over 1000, CNT are truly the ultimate additives for the fabrication of multifunctional composites. Their diameter is of the order of a few nanometers, and up to several millimeters in length. Carbon nanotubes can be divided into two general classes: single-walled (SWCNT-only one graphene sheet) and multi-walled (MWCNT-multiple graphene sheets nested into one another). It is generally agreed that for composite work, SWCNT are superior to MWCNT especially if multifunctionality is sought.

Due to the extended $sp^2$ hybridization network and their ability to form bundles, CNT are chemically very stable with poor compatibility with practically any solvents and matrices. To circumvent this problem, CNT need to be "chemically primed" to facilitate their integration and produce a good bonding interface. Chemical priming is achieved by anchoring of chemical functions at the surface. This invention refers to methods to integrate SWCNT in epoxy resins. The methods are applicable to CNTs of all kinds.

BRIEF REFERENCE TO THE PRIOR ART

Attachment of CNT to epoxide containing monomers and other chemical compounds including its polymers is a tedious, time consuming and costly process. Neutral CNT cannot be anchored directly to epoxide moieties. Chemical functionalization with suitable functional groups is necessary.

Currently, covalent attachment of CNT to epoxide containing species is done by first anchoring reactive functional groups such as —$NH_2$ or —COOH to the external wall of CNT and then subject the functionalized CNT to the epoxide containing species. The functionalization of CNT is lengthy and may require several steps. Two examples on how this may be accomplished are:

Example 1

Step 1: SWCNT+Li/$NH_3$→Li intercalated SWCNT
Step 2: Li intercalated SWCNT+X—R—NH-Fmoc→SWCNT-R—NH-Fmoc+LiX (X=Br, I)
Step 3: Hydrolyzation SWCNT-R—NH-Fmoc+piperidine→SWCNT-R—$NH_2$
Step 4: SWCNT-R—$NH_2$+Epoxy resin→SWCNT functionalized resins The origin of step 1 and similarly of step 2 can be found in the following paper: Liang et al., NanoLetters, 4, 1257 (2004).

Example 2

Step 1: SWCNT+HOOC—R—COO—OOC—R—COOH+heat→SWCNT-R—COOH+$CO_2$

Step 2: SWCNT-R—COOH+epoxy resin→SWCNT-R—COO—$CH_2$—CH(OH)—$CH_2$—. (esterification)

Steps 1 and 2 originate from work by Billups et al., Org. Lett., 5, 1471 (2003) and is not efficient but has been demonstrated by Margrave et al., Nanolett., 3, 1107 (2003).

Multi-step functionalization of neutral CNT works but it is time consuming and costly. The control over functionalization degree remains to be demonstrated. In addition, the effect of the chain length bearing the functional groups on the overall property of the composites is not known. Chemical functionalization is more costly than the production cost of CNT, especially for SWCNT.

SUMMARY OF THE INVENTION

There is provided herein materials and methods for modifications of CNTs. In an embodiment of the invention the nucleophilic character of negatively charged CNT is exploited to provide more efficient, more versatile and more control over the composite properties. This is achieved, in one embodiment, by priming the surface of the CNTs to induce negative charges thereon. In another embodiment it is achieved by reducing CNTs directly with radical anions produced by electron transfer from alkali metal to the acceptor molecules such as naphthalene and benzophenone.

BRIEF REFERENCE TO THE DRAWINGS

FIG. 11 of the accompanying drawings is a schematic drawing of a prior art process described by Matrab et. al., op. cit.;

FIG. 1 is a schematic drawing of the process of nucleophilic attack of CNT employed in one aspect of the present invention;

FIG. 2 is a diagrammatic illustration of a general procedure to prepare reduced CNT (Penicaud's method) useful in preparing starting materials for the present invention;

FIG. 3 is a diagrammatic presentation of an alternative procedure to prepare reduced CNT useful in preparing starting materials for the present invention;

FIG. 4 is a diagrammatic illustration of direct attachment of reduced CNT to epoxide functional groups in accordance with an embodiment of the invention;

FIG. 5 is a diagrammatic illustration of attachment of functionalized CNT to epoxy resins through base catalyzed ring opening, in accordance with another embodiment of the invention;

FIG. 6 is a diagrammatic illustration of a process of functionalizing CNT with a chain bearing a hydroxyl function, for subsequent use in an embodiment of the invention;

FIG. 7 is a diagrammatic illustration of an alternative process for functionalizing CNT with a chain bearing a hydroxyl function;

FIG. 8 is a diagrammatic illustration of a process of using negatively charged CNT as an initiator of polymerization, to make materials in accordance with the invention;

DESCRIPTION OF THE INVENTION

Nucleophilic attacks of CNT can be employed, for example as schematized in FIG. 1 of the accompanying drawings. CNT are primed to induce negative charges thereon, indicated by Nu-on FIG. 1. The CNT can be primed in one of two ways. In the first method, neutral CNT can be made to react with appropriate reagents to arrive at functionalized CNT in which negative charges are present. A second, presently preferred, method is to use reduced CNT. Reduced CNT can be prepared according to the method developed by Penicaud et al. (PCT application: WO 2005/073127: JACS 127, 8 (2005)). This method effectively charges up the CNT or its surroundings negatively by using radical anions. The reduced tubes thus acquire nucleophilic character. The general procedure to prepare reduced CNT with Penicaud's method is diagrammatically illustrated in accompanying FIG. 2.

Penicaud's procedure is carried out in THF and it has the advantage of dispersing the CNT at the single tube level or at least in very small bundles because of electrostatic repulsion between adjacent CNT. In some instances it will be desirable to use different solvents which are not practical and/or desirable for use with Penicaud's method. For example, toluene, ether, hexane and/or THF (tetrahydrofuran) can be employed when an approach is required which avoids the formation of naphthalene alkali complexes. In some instances it will be desirable to form alkali benzophenone complexes. Such complexes can be stabilized in toluene. In this example the electron donor is a benzophenone radical anion. An example of such a method is illustrated diagrammatically in accompanying FIG. 3.

Figure 10:
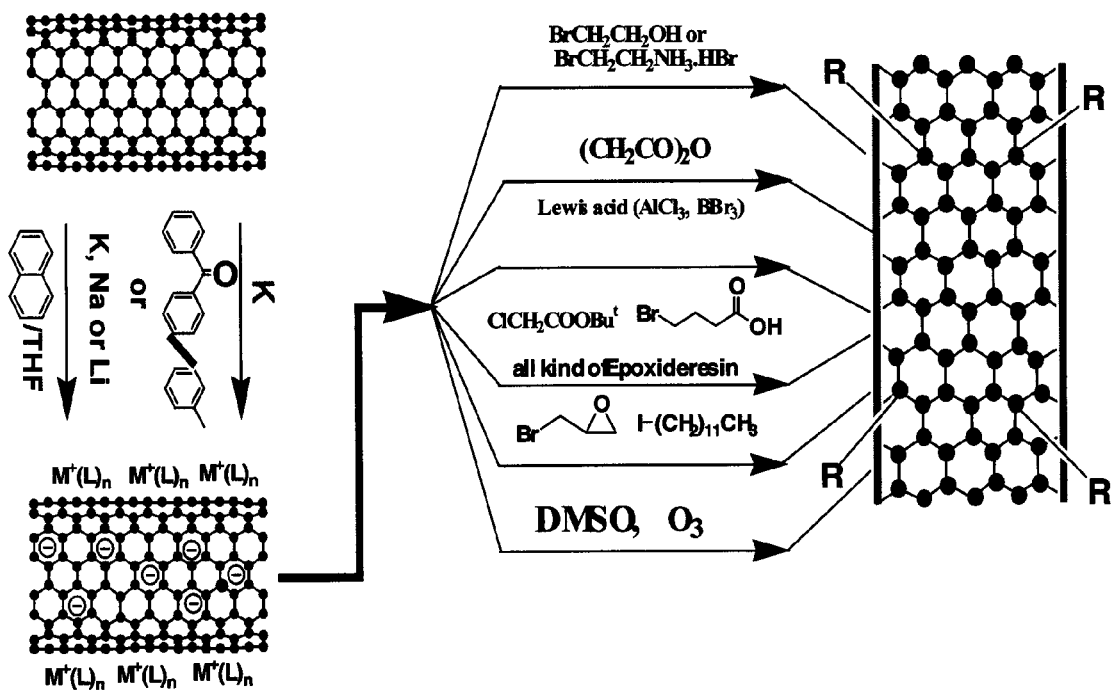
FIG. 10 is a schematic illustration of a process of reacting negatively charged (reduced) CNT with various functional groups in accordance with the invention.

Negatively charged (reduced) CNT can react with various functional groups as shown in FIG. 10.

Examples, depicting certain embodiments of methods to attach CNTs to epoxide functional group containing resins, are provided below:

Method 1: Direct Attachment of Reduced CNT to Epoxide Functional Groups.

As used in this example, the term "direct" indicates that the epoxide groups react directly with the partially negative carbon atoms making the side walls of CNT. The partial negative charge on each carbon atom forming the CNT results from electron transfer from the radical anions. Thus, there is no need for a "spacer" between the CNT wall and the epoxy resin backbone. An embodiment of this approach is depicted in FIG. 4.

It will be understood that the epoxide functional groups may be on any molecule with properties suited for its intended application. For example in the structure $\Delta_R$ (or, more generally "$F_1$—R—$F_2$" where "$F_1$" and "$F_2$" are the functional groups active in the depicted reaction), "R" can be alkyl, such as $C_1$-$C_{1000}$, $C_5$-$C_{500}$, $C_8$-$C_{100}$, $C_{15}$-$C_{50}$. R may be alkane, alkene, alkyne, linear or branched, or aromatic. It may include other functional groups and heteroatoms which do not significantly interfere with the desired reaction by $F_1$ and $F_2$.

In a typical experiment, 50 mg of SWCNTs (4.16 mmol of carbon) was ground with a mortar using a few drops of THF and then sonicated (Branson, model 5510 sonication bath) in 60 ml of dry THF until a well-dispersed suspension formed. Small pieces of sodium metal and naphthalene solid were added into the suspension through which $N_2$ was bubbled. The mixture was stirred overnight at room temperature and was visually characterized by its green color. Henceforth, this mixture will be called the Green solution. The reduced SWCNT were separated from the green solution by centrifugation under inert atmosphere. The reduced SWCNT were washed under inert atmosphere with dry THF twice to remove excess of sodium naphthalene salts and free naphthalene. The paste (or precipitate) of reduced SWCNTs was re-suspended in dry THF and mixed up with de-oxygenated (by sparging with Ar or $N_2$) epoxy resin MY0510 (triglycidyl-p-aminophenol resin, obtainable from Huntsman Chemical) under strong mechanical or magnetic stirring and under nitrogen or argon flow. The SWCNTs loading can range from 0 up to 10 wt % or higher. After mixing, the THF solvent was evaporated by sparging with strong Ar or $N_2$ flow. A very important aspect of this method is that the amount of cross linking and hence the final viscosity can be controlled by controlling the amount of oxidizing and hydrolyzing agents into the sample, which is done by sparging with wet air rather than inert atmosphere. Hence, the final product can be a viscous liquid, a rubbery solid or a solid depending on the sparging conditions used. This method affords the possibility of eliminating curing agents. Good control is exercised over the final product mixture.

It will be appreciated by those skilled in the art that these methods can also be employed to link CNTs to molecules having other functional groups instead of (or in addition to) epoxides. For example alkyl halides such as 1-Bromo(or Iodo)dodecane, 1-Bromoalcohol, 1-Bromoethylene amine, Bromo-carboxylic acid, Bromo-carboxylate ester, succinic anhydride, Epibromoanhydride, DMSO, and all kind of currently available commercial epoxy resins Here, the sample was prepared by sparging air into the sample. The moisture and oxygen from air effectively neutralized (oxidized) the reduced SWCNT and hydrolyzed the nucleophilic centers and thus terminate further cross-linking.

In an alternative finishing procedure, nitrogen and air were subsequently used to obtain a rubbery material. In another alternative, the sample was prepared absolutely under inert atmosphere and the final product was a solid.

Method 2: Attachment of Functionalized CNT to Epoxy Resins Through Base Catalyzed Ring Opening.

The general idea is to first functionalize neutral CNT with chains bearing hydroxyl functional groups which are then deprotonated with alkali metal to form alkoxides or aryloxides. Alkoxides and aryloxides are known to react readily with epoxide moieties. The difference with method 1 is that here the CNT are separated from the epoxy resin backbone by a spacer of fixed length.

As described with respect to Method 1, above, "R" may be any number of things in the structure CNT-R—OH. The following illustrative example validates the above method.

A suspension of 1.145 g (95.4 mmol) of SWCNT in 250 ml of 1,2-ODCB and 120 ml of acetonitrile was mixed with 2.3 equivalents of 4-aminobenzyl alcohol (27 g, 219.2 mmol) and 3 equivalents of isoamyl nitrite (33.5 g, 38.2 ml). The mixture was heated up to 70° C. over a weekend. After cooling down to around 50° C., the mixture was diluted with DMF and filtrated. The precipitate was washed with hot DMF and methanol a few times and dried. The scheme of this procedure is given in accompanying FIG. 6, and was first reported (Chem. Mat., 13, 3823 (2001) and described in the patent literature (US2005/0207963, WO 02/060812, GB 2412370) by Tour et al.

The resulting dry material, SWNT-$C_6H_4$—$CH_2OH$, was re-dispersed in dry THF by grinding and sonication technique, and a slight excess of Na was added. The mixture was stirred for a day. The mixture was added to a previously de-oxygenated sample of MY0510 and stirred vigorously. The quantity of resin was adjusted based on the requirement of the SWCNT loading by weight (0.2, 0.4% etc). The mixture was stirred for a day, then sparged with wet air or wet nitrogen to terminate the cross linking process and to evaporate the main part of the solvent (if the mixture was kept under nitrogen and barged with dry nitrogen, the resin will eventually solidify). Again, the procedure offers some control over the degree of cross-linking required. The remaining trace of solvent was completely removed in vacuum oven at 60° C. overnight.

It will be understood by those skilled in the art that this reaction is not limited to CNTs with —OH groups. For example, thiol functionalized CNTs may be used.

After nine months of ageing, a resin formulation prepared with this procedure retains very good dispersion and has not apparently changed over the months.

Hydroxyl functionalized SWCNT can also be prepared through the scheme illustrated diagrammatically in FIG. 7 and which is somewhat similar to: (NanoLett., 4, 1257 (2004)) and described in the patent literature by Billups et al., (WO 2005/090233).

Method 3: Block Functionalization of Reduced CNT Using Length Controllable Monomer, Oligomer or Polymers as Spacer.

This is based on the recognition that the negative charges in reduced CNT act as anionic initiator for polymerization of monomer such as styrene or methyl methacrylate (MMA) on CNT through the process known as grafting from, followed by termination through ring opening of the epoxide moieties provided by the epoxy resins. The general scheme with styrene is depicted in accompanying FIG. 8.

The following procedure validates the above concept.

8 ml of styrene and 8.5 g of MY0510 resin were added to a suspension of negatively charged SWCNTs obtained from a green solution by centrifugation and washing technique (see method 1). The mixture was shaken vigorously and sonicated, then further mixed on a Vortex-mixer for a few hours. The mixture was shaken for another two days, then diluted with THF. After centrifugation, the precipitate was washed with THF, $CHCl_3$ and THF a few times through a sonication-centrifugation cycle.

Method 4: Bi-Functionalization of Reduced CNT

Figure 9:
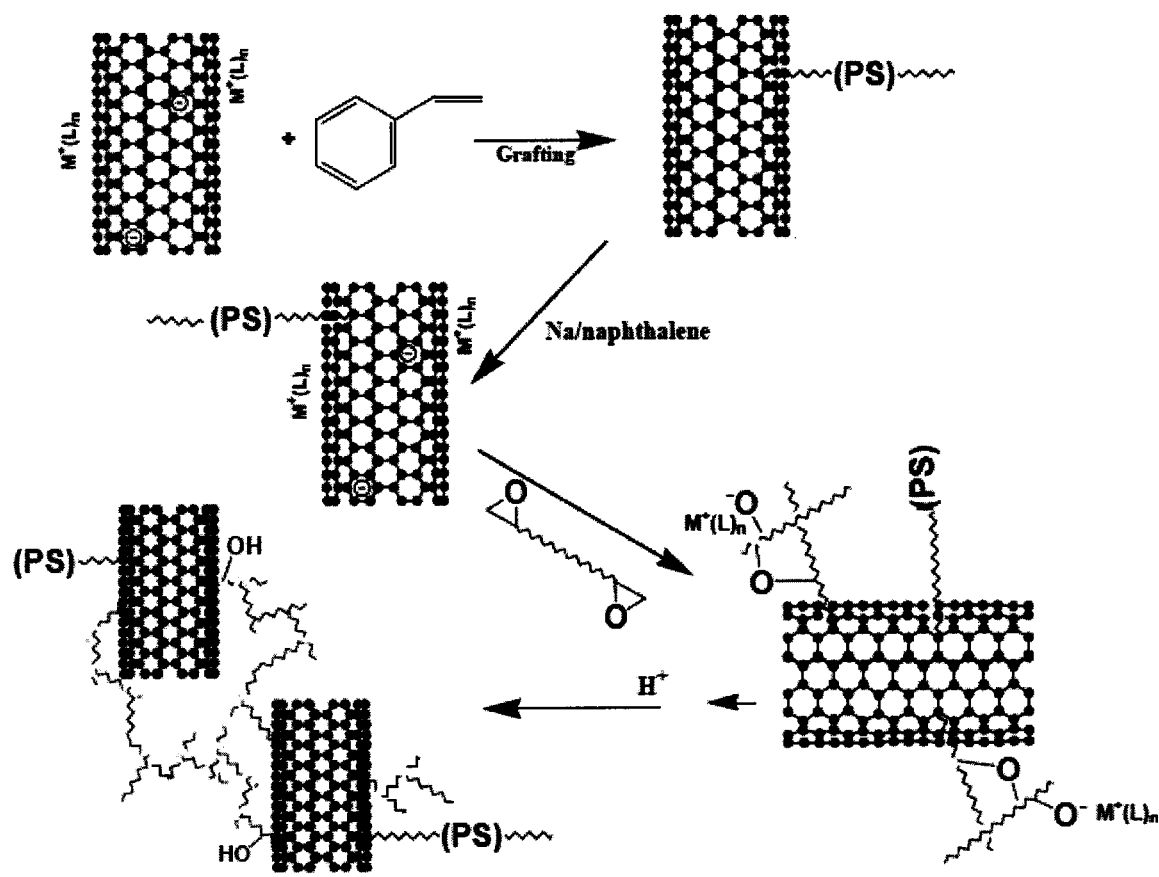
FIG. 9 is a diagrammatic illustration of a process of graft polymerization onto CNT followed by reaction thereof with epoxide moieties.

This can be considered as a two-step process. In the first step, polystyrene or PMMA is grafted from previously prepared reduced CNT. This produces polymer grafted CNT. In a second step, the polymer grafted CNT are reduced again and made to react with the epoxide moieties of epoxy resins. The second step is analogous to Method 1 described above except that the CNT used are polymer grafted. The overall process produces CNT with two independent functionalities, hence the term bi-functionalization. An example of the whole process in which styrene is used is depicted in accompanying FIG. 9.

The method described above provides materials with 1) better solubility in common solvents, 2) better dispersion properties in various epoxy formulations, and 3) more handles for property adjustment for composite formulations.

It will be understood by those skilled in the art that a wide range of monomers can be employed. Preferably, the monomer selected permits the easy formation of a radical through various initiation processes (photolysis, thermolysis). In some instances it will be desirable to use one or more of styrene, olefins, lactone and lactide as the selected grafting polymer.

There is disclosed herein:
1) Methods for the covalent attachment of CNT to epoxy resins through nucleophilic reactions with epoxide moieties.
2) Methods for the covalent attachment of reduced CNT to epoxy resins.
3) Methods for the covalent attachment of alkoxide functionalized CNT to epoxy resins.
4) A method for the reduction of CNT through electron transfer from benzophenone alkali salts in toluene
5) Methods for direct, spacer-free, covalent attachment of CNT to epoxy resins.
6) Methods for indirect, with fixed and variable length spacers, covalent attachment of CNT to epoxy resins
7) Methods for the preparation of CNT functionalized with two independent functional chains.
8) Methods for the preparation of CNT functionalized with two independent functional chains in which one chain is polystyrene or any other polymers dependent on the applications and the other an epoxy resin (monomer or polymer)
9) Methods for the preparation of CNT functionalized with two independent functional chains in which one chain is PMMA or any other polymers dependent on the applications and the other an epoxy resin (monomer or polymer).

What is claimed is:

1. A bi-functionalized carbon nanotube (CNT) having grafted thereon polymeric moieties of epoxy resin and polymeric moieties of olefins, lactones, lactides, or their derivatives.

2. A bi-functionalized CNT having grafted thereon polymeric moieties of epoxy resin and polymeric moieties of styrene and/or methylmethacrylate or methylmethacrylate derivatives.

* * * * *